United States Patent [19]

Nakamura et al.

[11] 4,243,747
[45] Jan. 6, 1981

[54] COLOR PHOTOGRAPHIC LIGHT-SENSITIVE MATERIAL

[75] Inventors: Kotaro Nakamura; Keiichi Adachi; Akira Ogawa, all of Minami-ashigara, Japan

[73] Assignee: Fuji Photo Film Co., Ltd., Minami-ashigara, Japan

[21] Appl. No.: 4,134

[22] Filed: Jan. 17, 1979

[30] Foreign Application Priority Data

Jan. 17, 1978 [JP] Japan ................................ 53-3451

[51] Int. Cl.³ ............................................. G03C 1/40
[52] U.S. Cl. ................................. 430/551; 430/554; 430/504
[58] Field of Search ................... 96/56, 95, 76, 77, 100

[56] References Cited

U.S. PATENT DOCUMENTS

| 3,907,571 | 9/1975 | Arai et al. | 96/56 |
| 3,930,866 | 1/1976 | Oishi et al. | 96/56 |
| 3,935,015 | 1/1976 | Arai et al. | 96/56 |
| 3,935,016 | 1/1976 | Nishimura et al. | 96/56 |
| 3,982,944 | 9/1976 | Ohi et al. | 96/56 |

Primary Examiner—Travis Brown
Attorney, Agent, or Firm—Sughrue, Rothwell, Mion, Zinn and Macpeak

[57] ABSTRACT

A color photographic light-sensitive material comprising a support having thereon a silver halide emulsion layer containing 2,5-bis(1',1'-dimethylbutyl)hydroquinone or a precursor thereof and a 3-anilino-5-pyrazolone type magenta coupler represented by the following general formula (II):

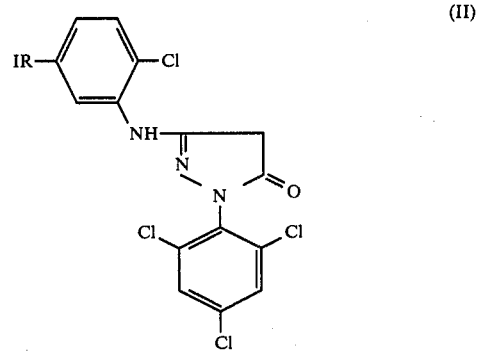

wherein IR represents RCONH—, RNHCO—, ROCO—, RNHSO$_2$—, ROSO$_2$NH—

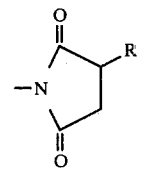

wherein R represents a hydrogen atom, an alkyl group having 1 to 35 carbon atoms, an alkenyl group or an aralkyl group, which groups can be further substituted.

The color photographic light-sensitive material can provide color images having excellent fastness and free from discoloration at the non-image areas.

12 Claims, No Drawings

COLOR PHOTOGRAPHIC LIGHT-SENSITIVE MATERIAL

BACKGROUND OF THE INVENTION

1. Field of the Invention

The present invention relates to a color photographic light-sensitive material and, more particularly, it relates to preventing fading of the dye images ultimately obtained by development processing a color photographic light-sensitive material and preventing discoloration of uncolored or white background areas.

2. Description of the Prior Art

Color photographic light-sensitive materials are subjected, after exposure, to a series of processing steps such as color development, bleaching, fixing, stabilizing, etc., to ultimately form color images.

Color photographic images thus-obtained are stored for a long period of time as records or to be displayed. However, these photographic images are not necessarily stable to light, humidity or heat and, when stored for a long period of time, the dye images tend to fade or discolor and, in addition, the white background is also discolored, which usually results in a deterioration of image quality. Such a phenomenon is enhanced when the dye images are exposed to light or stored under high temperature and high humidity conditions.

This fading and discoloration of images are fatal defects in a recording material. The following compounds have heretofore been used to remove these defects. For example, hydroquinone derivatives including 2,5-di-tert-butylhydroquinone, phenol compounds such as 2,6-di-tert-butyl-p-cresol, 4,4'-methylenebis(2,6-di-tert-butylphenol), 2,2'-methylenebis(4-ethyl-6-tert-butylphenol), 4,4'-isopropylidenediphenol, etc., and tocopherols are representative of such compounds.

These compounds are effective to some extent as fade preventing or discoloration preventing agents for dye images. However, the effect is not completely satisfactory, although some compounds may prevent fading, they deteriorate the hue, cause fog, reduce dispersion property or form crystals. Thus, satisfactory color image stabilizers which exhibit completely excellent effects for photographic use are not known.

Methods for overcoming these disadvantages are disclosed in Japanese Patent Application (OPI) No. 14023/1976 (The term "OPI" as used herein refers to a "published unexamined Japanese patent application)" in which a phenolic compound as described in U.S. Pat. Nos. 3,432,300, 3,573,050, 3,574,627 and 3,930,866, German Patent Application (OLS) Nos. 2,146,668 and 2,165,371 is used together with a hydroquinone derivative.

On the other hand, it is disclosed in U.S. Pat. No. 3,935,016 that magenta color images which can be stored with good stability when exposed to light are obtained by incorporating a certain 3-anilino-5-pyrazolone-type magenta coupler in combination with a hydroquinone having at least one substituent on the nucleus thereof and a total number of carbon atoms in the substituents being at least 8 into a color photographic light-sensitive material.

Although fading of dye images and discoloration of white background are certainly prevented by the abovedescribed methods in comparison with the prior art, it is desired to further improve these properties from practical standpoint.

SUMMARY OF THE INVENTION

Therefore, an object of the present invention is to provide a color photographic light-sensitive material which can provide a color photograph in which the fading of dye images and the discoloration of the white background are more fully prevented.

As a result of various investigations, it has now been discovered that the object of the present invention is effectively attained by the incorporation in a silver halide emulsion layer of a color photographic light-sensitive material of a certain 3-anilino-5-pyrazolone-type magenta coupler represented by the following general formula (II):

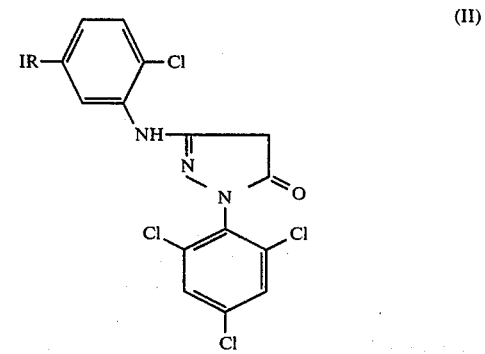

wherein IR represents RCONH—, RNHCO—, ROCO—, RNHSO$_2$—, RSO$_2$NH—

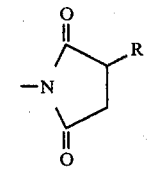

wherein R represents a hydrogen atom, an alkyl group, an alkenyl group or an aralkyl group, which groups can be further substituted, and 2,5-bis(1',1'-dimethylbutyl)-hydroquinone represented by the following formula (I) or a precursor thereof:

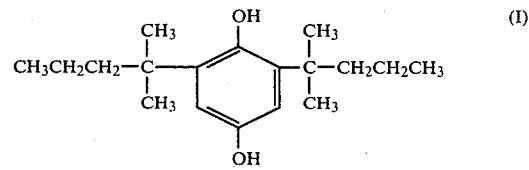

DETAILED DESCRIPTION OF THE INVENTION

The feature of the present invention is, namely, that the fading of dye images and the discoloration of white background are markedly prevented by the combination of certain 3-anilino-5-pyrazolone-type magenta cuuplers and a compound represented by the formula (I).

The compound of the formula (I) is disclosed in U.S. Pat. No. 3,982,944 and can be prepared by reference to that patent and its teachings.

The term "precursor" as used herein means a compound capable of releasing upon hydrolysis the hydroquinone of the formula (I) above. For example, a compound is considered a precursor when the hydrogen atom of one or both of the hydroxyl groups in the hydroquinone nucleus are substituted with an acyl group (with the term "acyl group" being used herein in its broad sense and including, for example,

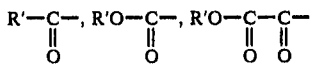

(wherein R' represents an aliphatic group such as an alkyl group), etc.).

As described above, the 3-anilino-5-pyrazolone-type magenta coupler according to the present invention is represented by the general formula (II), wherein IR represents RCONH—, RNHCO—, ROCO—, RNHSO$_2$—, RSO$_2$NH— or

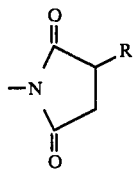

wherein R represents a hydrogen atom, a straight chain or branched chain alkyl group having 1 to 35 carbon atoms, preferably 1 to 22 carbon atoms (for example, a methyl group, an isopropyl group, a tert-butyl group, a hexyl group, a dodecyl group, a cyclopentyl group, a cyclohexyl group, a norbornyl group, etc.), a straight chain, branched chain or cyclic alkenyl group having 3 to 22 carbon atoms (for example, an allyl group, a cyclopentyl group, a cyclohexenyl group, etc.), or an aralkyl group having 7 to 22 carbon atoms wherein the aryl moiety may be a monocyclic or a bicyclic aryl group (for example, a benzyl group, a β-phenylethyl group, etc.).

These R groups can be substituted with one or more substituents selected from a halogen atom, a nitro group, a cyano group, an aryl group having 6 to 14 carbon atoms (e.g., phenyl, α-naphthyl), an alkoxy group having 1 to 10 carbon atoms (e.g., methoxy, ethoxy), an aryloxy group having 6 to 14 carbon atoms (e.g., phenoxy, α-naphthyloxy), a carboxy group, an alkylcarboxy group having 2 to 16 carbon atoms (e.g., acetyl, butyloyl), an arylcarbonyl group having 7 to 15 carbon atoms (e.g., benzoyl, α-naphthoyl), an alkoxycarbonyl group having 2 to 16 carbon atoms (e.g., methoxycarbonyl, ethoxycarbonyl), an aryloxycarbonyl group having 7 to 16 carbon atoms (e.g., phenoxycarbonyl, α-naphthoxycarbonyl), a formyl group, a sulfo group, an acyloxy group having 2 to 16 carbon atoms (e.g., acetyloxy, propionyloxy, benzoyloxy), a sulfamoyl group, a carbamoyl group, an acylamino group having 2 to 16 carbon atoms (e.g., acetylamino, butyloylamino, benzoylamino), a diacylamino group having 2 to 16 carbon atoms (e.g., diacetylamino), a ureido group, a thioureido group, a methane group, a thiourethane group, a sulfonamido group, a heterocyclic group containing 5 to 7 members wherein the hetero atoms may be oxygen, sulfur or nitrogen containing up to 3 hetero atoms in the ring, an arylsulfonyloxy group having 6 to 14 carbon atoms (e.g., phenylsulfonyloxy, α-naphthylsulfonyloxy), an alkylsulfonyloxy group having 1 to 16 carbon atoms (e.g., methanesulfonyloxy, ethanesulfonyloxy), an arylsulfonyl group having 6 to 16 carbon atoms (e.g., benzenesulfonyl, p-tolylsulfonyl), an alkylsulfonyl group having 1 to 16 carbon atoms (e.g., methanesulfonyl, ethanesulfonyl), an arylthio group having 6 to 16 carbon atoms (e.g., phenylthio, α-naphthylthio), an alkylthio group having 1 to 18 carbon atoms (e.g., methylthio, ethylthio), an alkylsulfinyl group having 1 to 16 carbon atoms (e.g., methylsulfinyl), an arylsulfinyl group having 6 to 16 carbon atoms (e.g., phenylsulfinyl), an alkylamino group having 1 to 16 carbon atoms (e.g., N-methylamino), dialkylamino group having 2 to 16 carbon atoms (e.g., N,N-dimethylamino), an anilino group, an N-arylanilino group having 12 to 16 carbon atoms (e.g., N-phenylanilino), an N-alkylanilino group having 7 to 16 carbon atoms (e.g., N-methylanilino), an N-acylanilino group having 8 to 16 carbon atoms (e.g., N-acetylanilino), a hydroxy group or a mercapto group. In the above substituents for R, any aryl moiety may be monocyclic or bicyclic and any alkyl moiety may be straight chain, branched chain or cyclic.

Specific examples of the compounds included in the general formula (II) are illustrated below but the magenta couplers which can be used in the present invention are not to be construed as being limited to these examples.

II-1

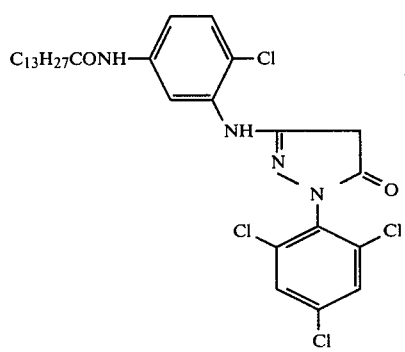

-continued
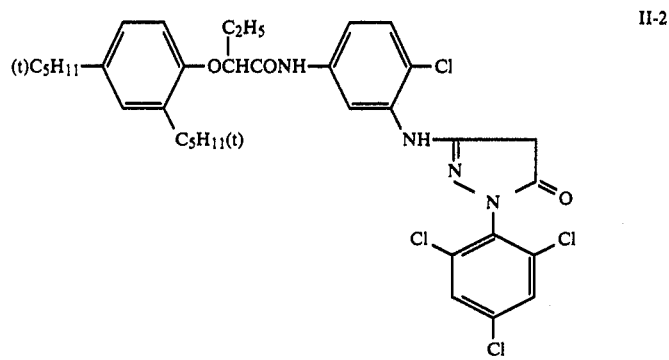
II-2
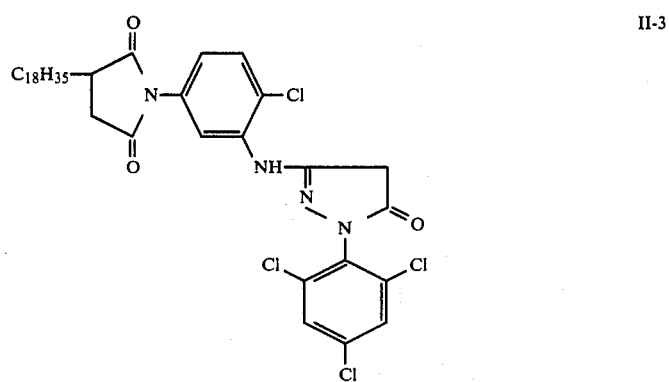
II-3
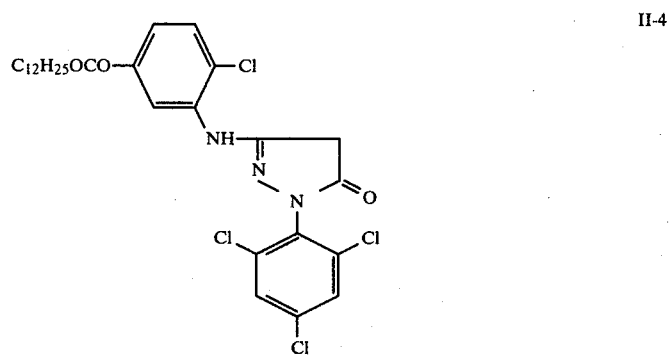
II-4
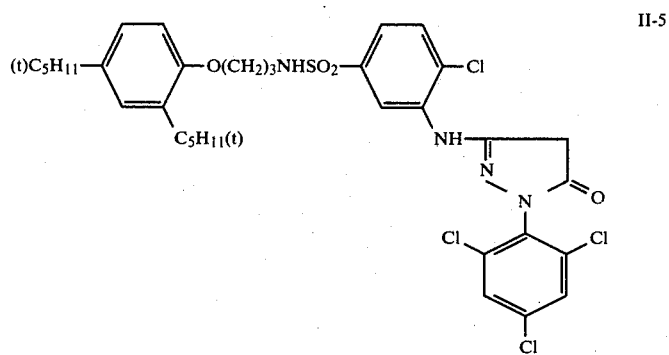
II-5

-continued
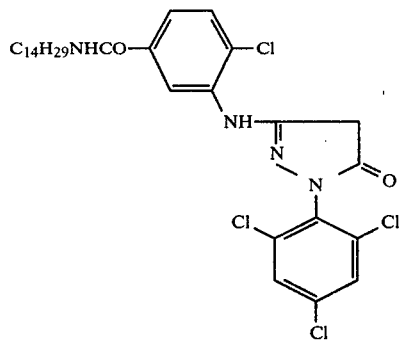
II-6
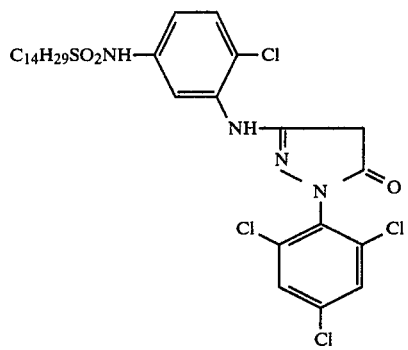
II-7
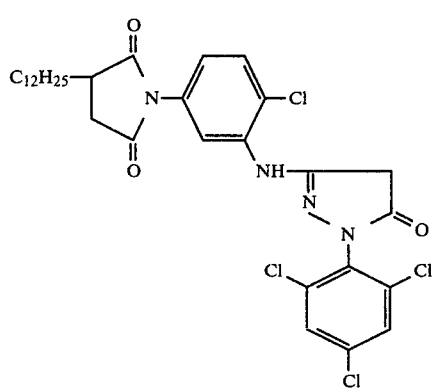
II-8
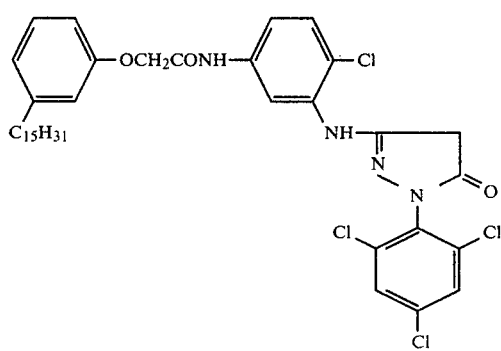
II-9

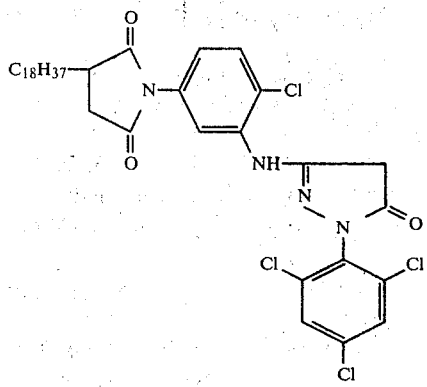

-continued

The above couplers can be synthesized by reference to well known procedures for synthesizing 3-anilino-5-pyrazolone couplers known in the art. For example, by reference to U.S. Pat. Nos. 3,935,015, 3,684,514, and 3,519,429.

The compound represented by the formula (I) and in the present invention can be suitably used in a range of about 0.5 to about 200 weight %, preferably 2 to 150 weight %, of the coupler of the general formula (II), although the amount thereof will depend on the specific coupler employed. If the amount is smaller than about 0.5 weight %, the effects of preventing light fading of the color image and of preventing the discoloration of white background are too small to be of practical use. On the other hand, if the amount is excessively large in comparison with that of the coupler, disadvantages may occur in that the color density obtained is decreased due to hindering color coupling.

In practicing the present invention, other known fading inhibiting agents can be used together therewith.

Examples of other known fading inhibiting agents are the hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921 and Japanese patent application No. 69148/1976, the gallic acid derivatives as described in U.S. Pat. Nos. 3,457,079 and 3,069,262 and Japanese Patent Publication No. 13496/1968.

Further, in practicing the present invention, it is more effective to employ therewith phenolic compounds having an ether bond at the 4-position thereof. Examples of phenolic compounds having an ether bond at the 4-position thereof which can be used in the present invention include alkoxyphenols, aryloxyphenols, hydroxycoumarans, hydroxychromans, dihydroxyspirochromans, etc., as described in U.S. Pat. Nos. 3,432,300, 3,573,050 and 3,574,627, and German patent application (OLS) Nos. 2,146,668 and 2,165,371, etc. These compounds may be used in the emulsion layer in coated amounts of 0.001 to 1.0 g/m² and preferably 0.01 to 0.5 g/m².

Preferred phenolic compounds are those compounds represented by the following general formulae (IIIa) to (IIIc):

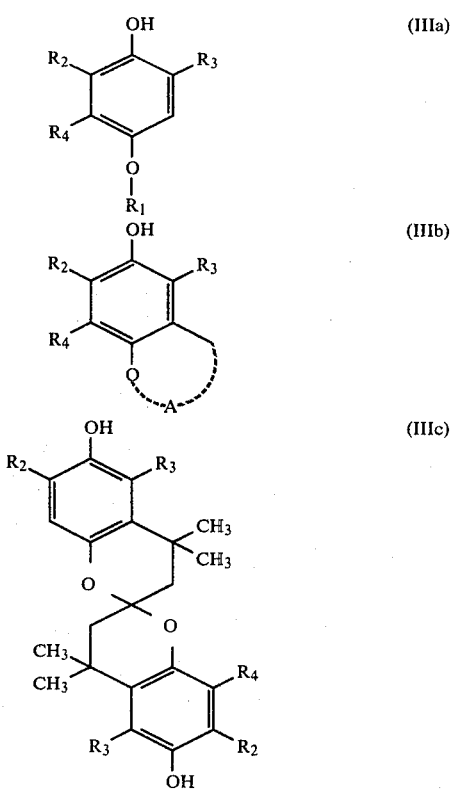

wherein $R_1$ represents a $C_1$ to $C_{22}$ alkyl group (such as a methyl group, a tert-butyl group, a hexyl group, an octyl group, a tertoctyl group, an octadecyl group, etc., a terpenyl group such as a 7,7-dimethylnorbornyl group, etc.), a $C_3$ to $C_{22}$ substituted alkyl group containing an alkoxy group, an alkylamino group, an alkylthio group, an alkoxycarbonyl group or a carbamoyl group as the substituent (such as a 1-ethoxycarbonyltridecyl group, 1-N-phenylcarbamoyltridecyl group, etc.), a $C_6$ to $C_{22}$ aryl group (such as a phenyl group, etc.) or a $C_7$ to $C_{22}$ aralkyl group (such as a benzyl group, phenethyl group, etc.); $R_2$, $R_3$ and $R_4$, which may be the same or different, each represents a hydrogen atom, alkyl group containing 1 to 18 carbon atoms (such as a methyl group, a tert-butyl group, a cyclopentyl group, a cyclohexyl group, an octyl group, a dodecyl group, an octadecyl group, etc.), an alkoxy group containing 1 to 18 carbon atoms (such as a methoxy group, a butoxy group, a dodecyloxy group, etc.), an alkylthio group containing 1 to 18 carbon atoms (such as an octylthio group, a hexadecylthio group, an octadecylthio group, etc.), an aryl group containing 6 to 14 carbon atoms (such as a phenyl group, etc.), an aryloxy group containing 6 to 14 carbon atoms (such as a phenoxy group, etc.), an aralkyl group containing 7 to 22 carbon atoms (such as a benzyl group, a phenethyl group, etc.), an aralkoxy group containing 7 to 22 carbon atoms (such as a benzyloxy group, a phenethyloxy group, etc.), an alkenyl group containing 3 to 22 carbon atoms (such as an allyl group, etc.), an alkenoxy group containing 3 to 22 carbon atoms (such as allyloxy group, etc.), an acylamino group containing 2 to 18 carbon atoms (such as an acetylamino group, a benzoylamino group, etc.), or a halogen atom (such as a chlorine atom, etc.); and A represents the non-metallic atoms necessary for completing a 5-membered or 6-membered ring containing a

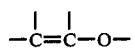

grouping and the ring can be substituted with an alkyl group containing 1 to 18 carbon atoms (such as a methyl group, a tert-butyl group, a cyclohexyl group, an octyl group, a dodecyl group, an octadecyl group, etc.), an alkoxy group containing 1 to 18 carbon atoms (such as a methoxy group, a butoxy group, a dodecyloxy group, etc.), an aryl group containing 6 to 14 carbon atoms (such as a phenyl group, etc.); an aryloxy group containing 6 to 14 carbon atoms (such as a phenoxy group, etc.), an aralkyl group containing 7 to 22 carbon atoms (such as a benzyl group, a phenethyl group, etc.), an aralkoxy group containing 7 to 22 carbon atoms (such as a benzyloxy group, a phenethyloxy group, etc.), an alkenyl group containing 3 to 22 carbon atoms (such as an allyl group, etc.), an alkenoxy group containing 3 to 22 carbon atoms (such as an allyloxy group, etc.), an N-substituted amino group containing 1 to 22 carbon atoms (such as an alkylamino group, a dialkylamino group, an N-alkyl-N-arylamino group, a piperazino group, a morpholino group, etc.), or a 5 to 7-membered heterocyclic ring containing up to 3 hetero atoms selected from oxygen, sulfur and nitrogen (such as a benzothiazolyl ring, a benzoxazolyl ring, an imidazolyl ring, an oxazolyl ring, etc.). Furthermore, the above-described ring can be substituted with a residue forming a condensed ring which is preferably an unsaturated ring containing 6 members (e.g., a benzene ring). Also, the alkyl group and the aryl group as described above for $R_1$ to $R_4$ and as substituents can be substituted with one or more of a halogen atom, a hydroxyl group, a carboxyl group, an alkoxycarbonyl group containing 2 to 16 carbon atoms, an acyloxy group containing 2 to 16 carbon atoms, a sulfo group, a sulfonyloxy group, an amido group (e.g., an acetamido group, an ethanesulfonamido group, a benzamido group, etc.), an alkoxy group or an aryloxy group.

The phenolic compounds of the general formula (IIIa) in which the total number of carbon atoms of $R_1$, $R_2$, $R_3$ and $R_4$ is 8 or more, the phenolic compounds of the general formula (IIIb) in which the total number of carbon atoms of $R_2$, $R_3$, $R_4$ and A is 8 or more, and the phenolic compounds of the general formula (IIIc) have the property of low diffusibility and hence are suitable for positioning selectively in a specific hydrophilic layer of the color photographic material. Also, the phenolic compounds having a total number of carbon atoms of up to about 40 are suitable for ordinary purposes.

The phenolic compounds which can be used in the present invention can be prepared according to the methods described, for example, in U.S. Pat. Nos. 2,535,058, 3,184,457, 3,285,937, 3,432,300, 3,573,050, 3,698,909, and 3,764,337, German Patent Application (OLS) Nos. 2,005,301, 2,008,376, 2,140,309, 2,146,668 and 2,165,371.

Furthermore, in practicing the present invention, it is also effective to use bisphenol derivatives in the emulsion layer. These compounds may be employed in amounts of 0.001 to 1.0 g/m² and preferably in amounts of 0.01 to 0.5 g/m². Examples of bisphenol derivatives are described in U.S. Pat. No. 3,700,455, Japanese patent Publication No. 31625/1973 and Japanese patent Application (OPI) No. 72225/1977, etc. Preferred bisphenol derivatives are those compounds represented by the following general formula (IV):

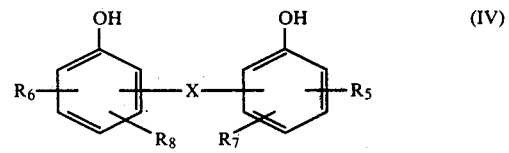

wherein $R_5$, $R_6$, $R_7$ and $R_8$ each represents an alkyl group having 1 to 18 carbon atoms and a total number of cation atoms in $R_5$, $R_6$, $R_7$ and $R_8$ is 32 or less; and X represents a single bond, an oxygen atom, a sulfur atom, a sulfonyl group or

wherein $R_9$ represents a hydrogen atom or an alkyl group having 1 to 10 carbon atoms and n represents an integer of 1 to 3.

These bisphenol compounds can be prepared according to the methods described, for example, in U.S. Pat. Nos. 2,792,428, 2,796,445, 2,841,619 and particularly 3,700,455, Japanese patent Publication No. 16539/1965, Japanese patent Application (OPI) No. 6338/1975, *Journal of the Chemical Society*, page 243 (1954).

Particularly useful examples of the phenolic compounds which can be used in the present invention are the 5-hydroxycoumarans and the 6-hydroxychromans which are compounds of the general formula (IIIb) where one of $R_2$ and $R_3$ is a hydrogen atom, the 6,6'-dihydroxy-bis-2,2'-spirochromans represented by the general formula (IIIc) and also bisphenols represented by the general formula (IV).

Specific examples of the compounds represented by the general formulae (IIIa), (IIIb), (IIIc) and (IV) are illustrated below but the compounds which can be used in the present invention are not to be construed as being limited to these examples.

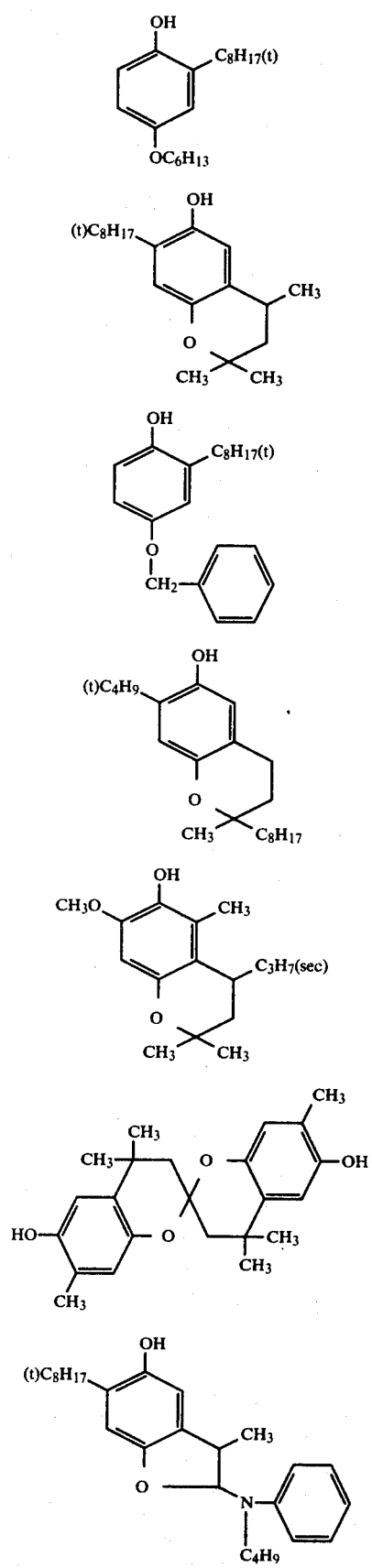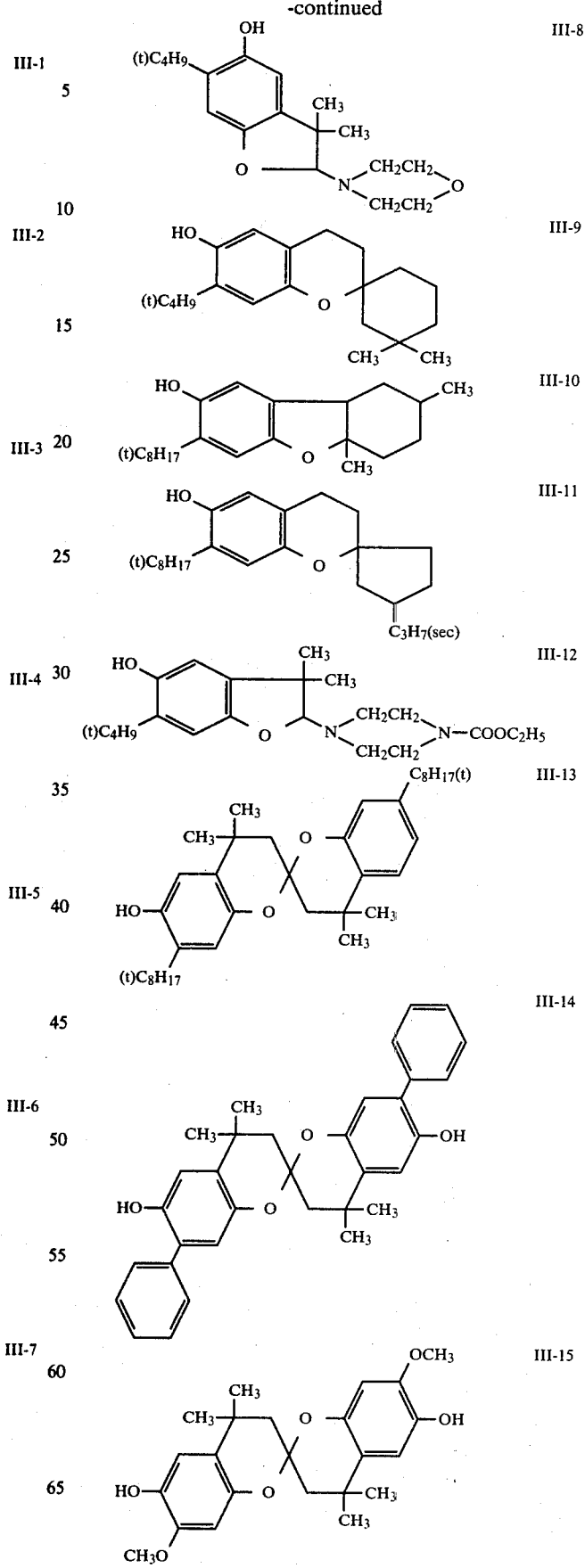

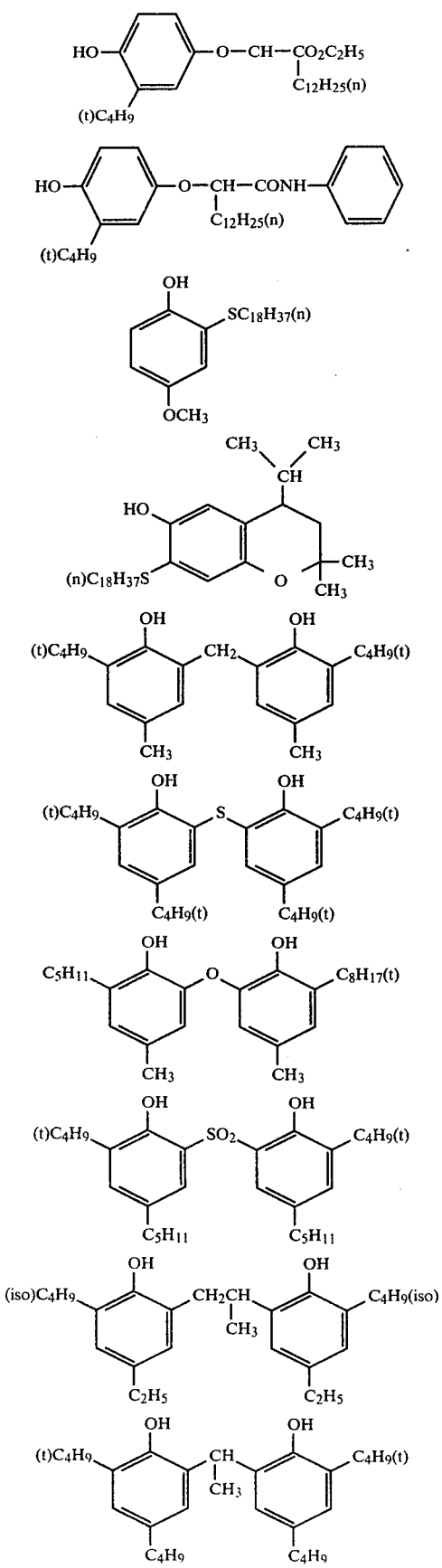

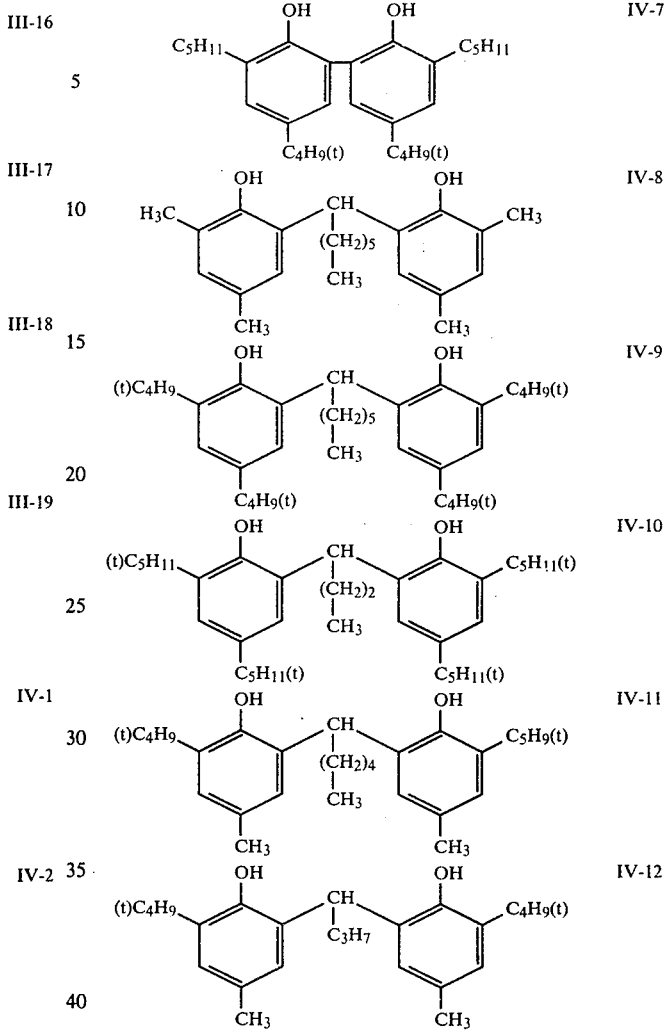

The compound represented by the formula (I) and the coupler represented by the general formula (II) which can be used in the present invention can be employed individually or as a combination thereof by dissolving them in a high boiling organic solvent with or without an auxiliary solvent and forming a dispersion thereof.

The high boiling organic solvent used in the present invention is an organic solvent which has a boiling point above 170° C. and which is immiscible with water. Typical examples of high boiling organic solvents include alkyl esters of phthalic acid (such as dibutyl phthalate, dioctyl phthalate, dinonyl phthalate, etc.), phosphoric acid esters (such as diphenyl phosphate, triphenyl phosphate, tricresyl phosphate, dioctyl butyl phosphate, trihexyl phosphate, etc.), citric acid esters (such as acetyl tributyl citrate, tributyl citrate, etc.), benzoic acid esters (such as butyl benzoate, octyl benzoate, etc.), alkylamides (such as diethyl laurylamide, etc.), sebacic acid esters (such as diethylhexyl sebacate, etc.), stearic acid esters (such as butyl stearate, etc.), maleic acid esters (such as dinonyl maleate, etc.), succinic acid esters (such as diethyl succinate, etc.), adipinic acid esters (such as dioctyl adipate, etc.), 3-ethylbiphenyl, the liquid dye stabilizers described, as improved photographic dye image stabilizers, in Product Licensing Index, Vol. 83, pp. 26 to 29 (March, 1971).

Examples of low boiling (about 30° to about 150° C. organic solvents which can be used as auxiliary solvents together with a high boiling organic solvent include lower alkyl acetates (such as ethyl acetate, butyl acetate, β-ethoxyethyl acetate, methyl Collosolve acetate, etc.), ethyl propionate, secondary butyl alcohol, methyl isobutyl ketone, ethyl formate, butyl formate, nitroethane, carbon tetrachloride, chloroform, hexane, cyclohexane, ethylene glycol, acetone, ethanol, dimethylformamide, dioxane, etc. In addition, benzene, toluene, xylene, etc., can also be used with these solvents. These solvents are described, for example, in U.S. Pat. Nos. 2,801,171, 2,801,170, and 2,949,360.

Surface active agents can also be used in dispersing a solution of the compound of the formula (I) individually or in combination with a coupler in an aqueous protective colloid solution. Illustrative examples of suitable surface active agents include saponin, sodium alkylsulfosuccinates, sodium alkylbenzenesulfonates, etc., and examples of hydrophilic protective colloids which can be used are those conventionally employed in photographic arts, for example, gelatin, casein, carboxymethyl cellulose, polyvinyl alcohol, polyvinyl pyrrolidone, styrene-maleic anhydride copolymers, condensates of styrene-maleic anhydride copolymers and polyvinyl alcohol, polyacrylic acid salts, ethyl cellulose, etc. However, the present invention is not to be construed to be limited only to these examples.

In order to incorporate the coupler into a silver halide emulsion layer, known methods, for example, the method described in U.S. Pat. No. 2,322,027, can be used. For example, a coupler is dissolved in a high boiling organic solvent described above, a low boiling organic solvent described above or a mixture thereof, the solution is dispersed into a hydrophilic protective colloid and the dispersion is mixed with a silver halide emulsion.

These couplers are generally used in an amount from about $2 \times 10^{-3}$ to about 2 mol, preferably from $1 \times 10^{-2}$ to $5 \times 10^{-1}$ mol, per mol of the silver in the emulsion layer.

Gelatin is advantageously used as the hydrophilic protective colloid which can be used in a photographic layer but other hydrophilic protective colloids can also be used. For example, a gelatin derivative, a graft polymer of gelatin and another polymer, a protein such as albumin, casein, etc., a cellulose derivative such as hydroxyethylcellulose, carboxymethylcellulose, cellulose sulfate, sodium alginate, a saccharide derivative such as a starch derivative and many kinds of synthetic hydrophilic high molecular weight materials such as a homopolymer or copolymer of polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc., are illustrative.

In addition to alkali treated gelatin, acid treated gelatin, a hydrolyzed product of gelatin, and an enzyme treated gelatin can be used as the gelatin.

Gelatin derivatives which can be used are those which are obtained by reacting gelatin with various kinds of compounds, for example, an acid halide, an acid anhydride, an isocyanate, a bromoacetic acid, an alkanesultone, a vinylsulfonamide, a maleinimide compound, a polyalkylene oxide, an epoxy compound. Specific examples of gelatin derivatives are described in U.S. Pat. Nos. 2,614,928, 3,132,945, 3,186,846 and 3,312,553, British Pat. Nos. 861,414, 1,033,189 and 1,005,784, Japanese patent publication No. 26845/1967, etc.

Gelatin graft polymers which can be used are those which are obtained by grafting a polymer or copolymer of vinyl monomers such as acrylic acid, methacrylic acid, or an ester or an amide derivative thereof, acrylonitrile, styrene, etc., to gelatin. Particularly preferred polymers are those compatible with gelatin to some extent, e.g., polymers of acrylic acid, methacrylic acid, acrylamide, methacrylamide, and hydroxyalkyl methacrylates, etc. Examples of these compounds are described in U.S. Pat. Nos. 2,763,625, 2,831,767 and 2,956,884, etc.

Typical synthetic hydrophilic high molecular weight materials are described, for example, in German Patent Application (OLS) No. 2,312,708, U.S. Pat. Nos. 3,620,751 and 3,879,205, Japanese patent publication No. 7561/1968, etc.

The photographic emulsion used in the present invention can contain any silver halide such as silver bromide, silver iodobromide, silver iodochlorobromide, silver chlorobromide and silver chloride.

The grain size distribution can be narrow or broad. The silver halide grains in the photographic emulsion can have a regular crystal form such as that of a cubic or octahedral system, an irregular crystal form such as that of a spherical or plate-like system, or can be a mixed system thereof. A mixture of grains having various kinds of crystal forms can be used.

The crystal structure of the silver halide grains can be uniform throughout the grains, or can be heterogeneous with the interior and the exterior differing from each other. Further, the silver halide grains can be of the type which forms a latent image predominantly on the surface of the grains or can be of the type which forms a latent image predominantly in the interior of the grains.

The photographic emulsion used in the present invention can be prepared using the methods described in P. Grafkides, *Chimie et Physique Photographique*, Paul Montel, Paris (1967), G. F. Duffin, *Photographic Emulsion Chemistry*, The Focal Press, London (1966), V. L. Zelikman, et al., *Making and Coating Photographic Emulsions*, The Focal Press, London (1964), etc. That is, the emulsion can be prepared using an acid process, a neutral process or an ammonia process. Further, any system for mixing a water-soluble silver salt and a water-soluble halide, such as a single jet adding method, a double jet adding method, a mixture thereof can be used.

A method in which the silver halide grains are formed in the presence of excess silver ion (the so-called reverse mixing method) can also be used. A method of the double jet adding method in which the pAg of the liquid phase wherein the silver halide grains are formed is maintained at constant, i.e., the so-called controlled double jet method can be used. According to this method, a silver halide emulsion containing silver halide grains having a regular crystal form and a homogeneous grain size distribution can be obtained.

Also, two or more silver halide emulsions which are prepared separately can be used in mixture, if desired.

During the preparation of the silver halide grains or the process of physical ripening, a cadmium salt, a zinc salt, a lead salt, a thallium salt, an iridium salt, a complex salt thereof, a rhodium salt, a complex salt thereof, an iron salt, a complex salt thereof can be present.

In the production of the photographic light-sensitive materials according to the present invention, a photographic emulsion layer and other hydrophilic colloid layers can be coated on a support or on another layer using various known coating methods including dip coating, roller coating, curtain coating, extrusion coating, etc. The methods described in U.S. Pat. Nos. 2,681,294, 2,761,791 and 3,526,528 can be advantageously used.

Suitable supports which can be used in the present invention include those which are commonly used for photographic light-sensitive materials such as a cellulose nitrate film, a cellulose acetate film, a cellulose acetate butyrate film, a cellulose acetate propionate film, a polystyrene film, a polyethylene terephthalate film, a polycarbonate film, a laminate of these films, a thin glass film, paper, and the like. Papers coated or laminated with baryta or an α-olefin polymer, in particular, a polymer of an α-olefin having 2 to 10 carbon atoms, such as polyethylene, polypropylene, an ethylene-butene copolymer, etc., synthetic resin films whose surface has been roughened to improve the adhesive property with other polymers as described in Japanese patent publication No. 19068/1972 also provide good results.

Suitable supports include transparent or opaque supports which are selected depending upon the end-use of the light-sensitive materials. Also, transparent supports colored with a dye or pigment can be used as well.

In practicing the present invention, it is naturally additionally effective and advantageous to prevent fading or discoloration by light to provide an ultraviolet light-absorbing layer on the upper surface of a photographic light-sensitive image-forming layer upon coating on a support.

The present invention is not limited by the kinds of conventionally used color processing agents such as color developing agents, bleaching agents, fixing agents, etc. Also, the present invention is not limited by the kind of intensifying agents to be used for color intensifying processing, e.g., as described in German patent application (OLS) No. 181,390, Japanese patent application (OPI) No. 9728/1973, Japanese patent application No. 128327/1974, etc.

The present invention is applicable to conventional color light-sensitive materials, in particular, to color light-sensitive materials for printing. Also, it is applicable to silver-saving type color light-sensitive materials described in U.S. Pat. Nos. 3,765,890, 3,902,905, 3,674,490 and 3,761,265, etc. Further, the present invention is applicable to the color photographic system described in U.S. Pat. Nos. 3,227,550, 3,227,551, 3,227,552, U.S. Provisional Patent Publication No. 351,673, etc., in particular, to the color diffusion transfer photographic system.

Color photographic development processing is necessary after exposure in order to obtain dye images using the color photographic light-sensitive material of the present invention. Color photographic development processing fundamentally involves a color developing step, a bleaching step, and a fixing step. In some cases, two of these steps can be conducted in a single processing. In addition, a combination of a color development, a first fixing and a bleach-fixing is also possible. The development processing step is combined with, if necessary, a prehardening bath, a neutralizing bath, a first development (black-and-white development), an image-stabilizing bath, a washing or the like. A suitable processing temperature is in many cases about 18° C. or above. Particularly, the processing temperature can be about 20° C. to 60° C., and more recently about 30° C. to about 60° C.

A suitable color developer solution which can be used in an alkaline aqueous solution having a pH of about 8 or higher, preferably 9 to 12, containing a color developing agent. Preferred typical examples of the above-described color developing agent are 4-amino-N,N-diethylanilane, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and the salts thereof (e.g., sulfates, hydrochlorides, sulfites, p-toluenesulfonates, etc.). Other examples are described in U.S. Pat. Nos. 2,193,015, 2,592,364, Japanese patent application (OPI) No. 64933/1973, L. F. A. Mason, *Photographic Processing Chemistry*, pp. 226–229, Focal Press, London (1966), etc. The above-described compounds may be used together with 3-pyrazolidones, if desired.

If desired, various additives may be added to the color developer solution.

The color developer solution can further contain pH buffers such as alkali metal sulfites, carbonates, borates or phosphates, development inhibitors or anti-fogging agents such as bromides, iodides or organic anti-fogging agents.

Specific examples of anti-fogging agents include potassium bromide, potassium iodide, nitrobenzimidazoles described in U.S. Pat. Nos. 2,496,940 and 2,656,271, mercaptobenzimidazole, 5-methylbenzotriazole, 1-phenyl-5-mercaptotetrazole, the compounds described in U.S. Pat. Nos. 3,113,864, 3,342,596, 3,295,976, 3,615,522, 3,597,119, etc., the thiosulfonyl compounds described in British Pat. No. 972,211, the phenazine-N-oxides as described in Japanese patent publication No. 41675/1971, the anti-fogging agents described in *Kagaku Shashin Binran*, Vol. II, pp. 29–47, and the like.

In addition, the color developer may contain, if desired, a water softener, a preservative such as hydroxylamine, an organic solvent such as benzyl alcohol, diethylene glycol, etc., a development accelerator such as polyethylene glycol, a quaternary ammonium salt, an amine, etc., a dye-forming coupler, a competing coupler, a fogging agent such as sodium borohydride, an auxiliary developing agent such as 1-phenyl-3-pyrazolidone, a viscosity-imparting agent, and the like.

After color development processing, the photographic emulsion layer is usually subjected to bleaching. Bleaching may be conducted either simultaneously with fixing or independently thereof. Suitable bleaching agents which can be used include compounds of multivalent metals such as iron (III), cobalt (III), chromium (VI), copper (II), etc., peracids, quinones, nitroso compounds, etc. For example, ferricyanides, dichromates, organic complex salts of iron (III) or cobalt (III), complex salts of aminopolycarboxylic acids (e.g., ethylenediaminetetraacetic acid, nitrilotriacetic acid, 1,3-diamino-2-propanoltetraacetic acid, etc.) or of organic acids (e.g., citric acid, tartaric acid, malic acid, etc.), persulfates, permanganates, nitrosophenol, etc., can be used. Of these, potassium ferricyanide, iron (III) sodium ethylenediaminetetraacetate and iron (III) ammonium ethylenediaminetetraacetate are particularly useful. Ethylenediaminetetraacetic acid-iron (III) complex salt is effective in a bleaching solution and in a monobath bleach-fixing solution.

Various additives including the bleaching-accelerators described in U.S. Pat. Nos. 3,042,520, 3,241,966, Japanese patent publication Nos. 8506/1970, 8836/1970, etc., can be added to the bleaching solution or bleach-fixing solution.

The present invention is illustrated in greater detail by reference to the following typical examples thereof. Unless otherwise indicated, all parts, percents, ratios, etc., are by weight.

EXAMPLE 1

10 g of Compound (II-1) as a magenta coupler was dissolved in a mixture of 10 ml of tricresyl phosphate and 20 ml of ethyl acetate, and the resulting solution was dispersed in 80 g of a 10% gelatin aqueous solution containing 5 ml of a 1% solution of sodium dodecylbenzenesulfonate. Then, this dispersion was mixed with 145 g of a green-sensitive silver chlorobromide emulsion (bromide content: 50 mol%) containing 7 g of silver and the emulsion was coated on a paper support, both sides of which had been laminated with polyethylene, and dried. The coated amount was 200 mg/m$^2$ based on the coupler.

On the emulsion layer a gelatin protective layer was coated (gelatin: 1 g/m$^2$) to prepare Sample A.

In the same manner, Samples B, C and D were prepared. In Sample B, 0.9 g of a compound represented by the formula (I) was further added to a solution containing the magenta coupler, tricresyl phosphate and ethyl acetate. For Sample C, 0.7 g of 2-tert-octyl hydroquinone, a comparison compound, was added in place of the compound of the formula (I). In Sample D, 1.1 g of 2,5-di-tert-octyl hydroquinone, another comparison compound, was added in place of the compound of the formula (I).

Samples A to D were then exposed to light of 1,000 lux for 1 second using a sensitometer and subjected to the following processing.

| Processing Step | Temperature (°C.) | Time |
|---|---|---|
| Color Development | 33 | 3 min 30 sec |
| Bleach-Fixing | 33 | 1 min 30 sec |
| Washing | 30 | 3 min |
| Drying | | |

The processing solutions used had the following compositions.

| Color Developer Solution | |
|---|---|
| Benzyl Alcohol | 15 ml |
| Sodium Sulfite | 5 g |
| Potassium Bromide | 0.5 g |
| Hydroxylamine Sulfate | 3 g |
| 4-(N-Ethyl-N-β-methanesulfonamido-ethylamino)-2-methylaniline Sesquisulfate | 6 g |
| Sodium Carbonate (monohydrate) | 28 g |
| Water to make | 1,000 ml |
| | (pH 10.1) |
| Bleach-Fixing Solution | |
| Ferric Salt of Ethylenediamine- | 45 g |

| -continued | |
|---|---|
| tetraacetic Acid | |
| Sodium Sulfite | 10 g |
| Ammonium Thiosulfate (70% aq. soln.) | 160 ml |
| Tetrasodium Ethylenediaminetetraacetate | 5 g |
| Water to make | 1,000 ml |
| | (pH 6.8) |

Each of Samples A to D thus-processed was subjected to a fading test for 2 weeks using a fluorescent lamp fading tester (20,000 lux) equipped with an ultraviolet light-absorbing filter absorbing light of a wavelength of 400 nm or shorter (C-40, made by the Fuji Photo Film Co., Ltd.). The results obtained are shown in Table 1 below for an area in which the initial density was 2.0.

TABLE 1

| Sample | Magenta Density after Fading Test (Initial Density: 2.0) |
|---|---|
| A | 0.29 |
| B | 1.85 |
| C | 1.01 |
| D | 1.48 |

From the results shown in Table 1 above, it is apparent that the magenta dye image in Sample B in which the compound represented by the formula (I) is used according to the present invention exhibits a superior light-fastness in comparison to Samples C and D in which comparison compounds were used. This shows the unusual characteristic of the compound of the formula (I) and which is unexpected and surprising. The density was measured by a Macbeth densitometer.

EXAMPLE 2

Sample E was prepared in the same manner as Sample B of Example 1 but 1.1 g of phenolic Compound (III-6) was further added. Sample F was prepared in the same manner as Sample E but using 5.5 g of Compound (IV-1) in place of Compound (III-6), for comparison. Sample G was prepared in the same manner as Sample D of Example 1 but 1.1 g of phenolic Compound (III-6) was further added. Sample H was prepared in the same manner as Sample G but using 5.5 g of Compound (IV-1) in place of Compound (III-6).

Samples E to H and Sample A were exposed and processed in the same manner as described in Example 1. Then, Samples E to H and Sample A thus-processed were subjected to a fading test for 1 week using a xenon lamp fading tester (200,000 lux) equipped with an ultraviolet light-absorbing filter absorbing light of a wavelength of 400 nm or shorter (C-40, made by the Fuji Photo Film Co., Ltd.). The density was measured by a Macbeth densitometer. The results obtained are shown in Table 2 below.

TABLE 2

| Sample | Magenta Density after Fading Test. (Initial Density: 2.0) |
|---|---|
| E | 1.82 |
| F | 1.68 |
| G | 1.60 |
| H | 1.45 |
| A | 0.20 |

From the results shown in Table 2 above, it is recognized that the compound represented by the formula (I) of the present invention shows further improved light-fastness of magenta dye image when it is used together with the phenolic compound or the bisphenol compound. Also, in the combined use of the phenolic compound or the bisphenol compound, improvement in the light-fastness is highly observed with the compound of the formula (I) according to the present invention in comparison with the above-described comparison compounds.

EXAMPLE 3

The coating composition for the third layer shown in Table 3 below was prepared in a similar manner described in Sample A of Example 1 using Compound (II-1) as a magenta coupler. A multi-layer sample as shown in Table 3 below containing the third layer described above was prepared (Sample W). Also, Sample X and Sample Y were prepared in the same manner as Sample W but additionally using 0.9 g and 1.8 g of the compound of the formula (I) according to the present invention per 10 g of the coupler in the coating composition for the third layer, respectively. Further, for comparison, Sample Z was prepared in the same manner as Sample X but using 1.1 g of 2,5-di-tert-octyl hydroquinone in place of the compound of the formula (I).

TABLE 3

| | |
|---|---|
| Sixth Layer: (protective layer) | Gelatin 1,000 mg/m$^2$ |
| Fifth Layer: (red-sensitive layer) | Silver chlorobromide emulsion (Br: 50 mol %) Silver 300 mg/m$^2$; Cyan coupler, 2-[α-(2,4-Di-tert-pentylphenoxy)butanamido]-4,6-dichloro-5-methylphenol, 400 mg/m$^2$; Gelatin 1,000 mg/m$^2$; Coupler solvent, Dibutyl phthalate, 200 mg/m$^2$ |
| Fourth Layer: (intermediate layer) | Gelatin 1,200 mg/m$^2$; Ultraviolet light-absorbing agent, 2-(2-Hydroxy-3-sec-butyl-5-tert-butylphenyl)benzotriazole, 1,000 mg/m$^2$; Ultraviolet absorbing agent solvent, Dibutyl phthalate, 250 mg/m$^2$ |
| Third Layer: (green-sensitive layer) | Silver chlorobromide emulsion (Br: 50 mol %) Silver 290 mg/m$^2$; Magenta coupler, 1-(2,4,6-Trichlorophenyl)-3-(2-chloro-5-tetradecan-amido)anilino-2-pyrazolin-5-one, 200 mg/m$^2$; Coupler solvent, Tricresyl phosphate, 200 mg/m$^2$; Gelatin 1,000 mg/m$^2$ |
| Second Layer: (intermediate layer) | Gelatin 1,000 mg/m$^2$ |
| First Layer: (blue-sensitive layer) | Silver chlorobromide emulsion (Br: 80 mol %) Silver 400 mg/m$^2$; Gelatin 1,200 mg/m$^2$; Yellow coupler, α-Pivaloyl-α-(2,4-dioxo-5,5'-dimethyloxazolidin-3-yl)-2-chloro-5-[α-(2,4-di-tert-pentylphenoxy)butanamido]acetanilide, 300 mg/m$^2$; Coupler solvent, Dioctyl butyl phosphate, 150 mg/m$^2$ |
| Support: | Paper, both sides of which were laminated with polyethylene |

(In the table, the designation "mg/m$^2$" is the amount coated.)

These samples were exposed through a light wedge with a green filter (SP-2, made by the Fuji Photo Film Co., Ltd.) at 1,000 lux for 1 second and processed in the same manner as described in Example 1. The samples thus-processed were subjected to the fading test for 3 weeks using a fluorescent lamp fading tester (200,000 lux). The density was measured by a Macbeth densitometer. The results obtained are shown in Table 4 below.

TABLE 4

| Sample | Magenta Density after Fading Test (initial density: 2.0) | Yellow Density in Background Areas after Fading Test |
|---|---|---|
| W | 0.58 | 0.32 |

TABLE 4-continued

| Sample | Magenta Density after Fading Test (initial density: 2.0) | Yellow Density in Background Areas after Fading Test |
|---|---|---|
| X | 1.85 | 0.27 |
| Y | 1.91 | 0.21 |
| Z | 1.57 | 0.30 |

From the results shown in Table 4 above, it is apparent that the compound of the formula (I) according to the present invention exhibits a superior light fastness of magenta dye image in a multi-layer sample. Further, it should be noted that yellow stain in the background areas which occurs on exposure the sample to light is prevented and that the fading preventing effect and stain preventing effect are both increased as the increase of the amount of the compound of the formula (I) used.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having thereon a silver halide emulsion layer containing 2,5-bis(1',1'-dimethylbutyl)hydroquinone or a precursor thereof and a 3-anilino-5-pyrazolone type magenta coupler represented by the following general formula (II):

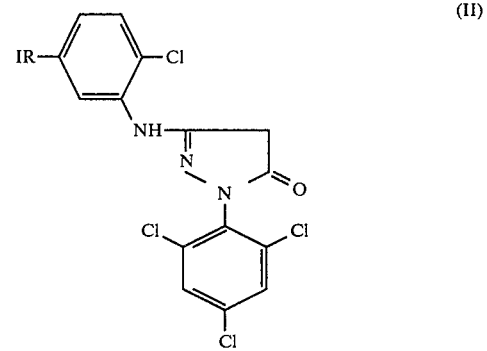

wherein IR represents RCONH—, RNHCO—, ROCO—, RNHSO$_2$—, RSO$_2$NH—

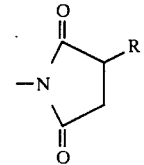

wherein R represents a hydrogen atom, an alkyl group, an alkenyl group or an aralkyl group, which groups can be substituted or unsubstituted.

2. The color photographic light-sensitive material of claim 1, wherein the R group substituent is one or more of a halogen atom, a nitro group, a cyano group, an aryl group, an alkoxy, an aryloxy group, a carboxy group, an alkylcarbonyl group, an arylcarbonyl group, an alkoxycarbonyl group, an aryloxycarbonyl group, a formyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group.

3. The color photographic light-sensitive material of claim 1, wherein said silver halide emulsion layer further contains a phenolic compound having an ether bond at the 4-position.

4. The color photographic light-sensitive material of claim 3, wherein said phenolic compound is an alkoxyphenol, an aryloxyphenol, a hydroxycoumaran, a hydroxychroman or a dihydroxyspirochroman.

5. The color photographic light-sensitive material of claim 3, wherein said phenolic compound is a compound represented by the following general formula (IIIa), (IIIb) or (IIIc):

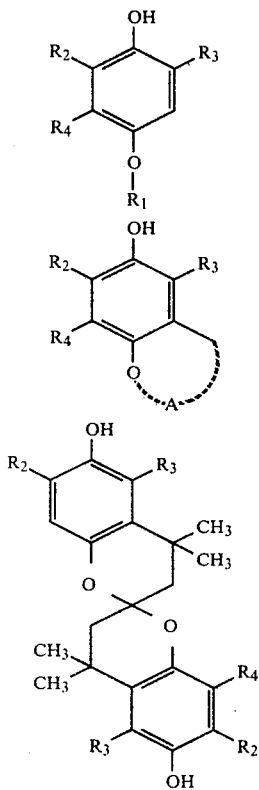

wherein $R_1$ represents an alkyl group, a substituted alkyl group, an aryl group or an aralkyl group; $R_2$, $R_3$ and $R_4$, which may be the same or different, each represents a hydrogen atom, an alkyl group, an alkoxy group, a thioalkyl group, an aryl group, an aryloxy group, an aralkyl group, an aralkoxy group, an alkenyl group, an alkenoxy group, an acylamino or a halogen atom; and A represents the non-metallic atoms necessary to complete a 5-membered or 6-membered ring containing a

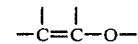

grouping and the ring can be substituted with an alkyl group, an alkoxy group, an aryl group, an aryloxy group, an aralkyl group, an aralkoxy group, an alkenyl group, an alkenoxy group, an N-substituted amino group or a heterocyclic group, which may be substituted with a residue forming a condensed ring; and wherein the alkyl group and the aryl group as described above for $R_1$ and $R_4$ can be substituted with one or more of a halogen atom, a hydroxyl group, a carboxyl group, an alkoxycarbonyl group, an acyloxy group, a sulfo group, a sulfonyloxy group, an amido group, an alkoxy group or an aryloxy group.

6. The color photographic light-sensitive material of claim 5, wherein said phenolic compound is a 5-hydroxycoumaran or a 6-hydroxychroman having the general formula (IIIb) wherein one of $R_2$ and $R_3$ is a hydrogen atom or a 6,6'-dihydroxy-bis-2,2'-spirochroman having the general formula (IIIc).

7. The color photographic light-sensitive material of claim 1, wherein said silver halide emulsion layer further contains a bisphenol derivative represented by the following general formula (IV):

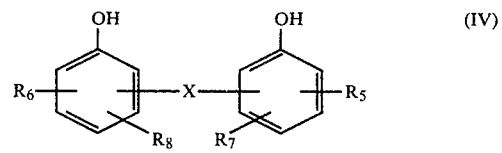

wherein $R_5$, $R_6$, $R_7$ and $R_8$ each represents an alkyl group having 1 to 18 carbon atoms and the total number of carbon atoms in $R_5$, $R_6$, $R_7$ and $R_8$ is 32 or less, and X represents a single bond, an oxygen atom, a sulfur atom, a sulphonyl group or

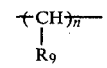

wherein $R_9$ represents a hydrogen atom or an alkyl group having 1 to 10 carbon atoms and n represents an integer of 1 to 3.

8. The color photographic light-sensitive material of claim 1, wherein said hydroquinone is present in an amount of about 0.5 to about 200% by weight based on the weight of said magenta coupler of the general formula (II).

9. The color photographic light-sensitive material of claim 8, wherein said hydroquinone is present in an amount of 2 to 150% by weight based on the weight of said magenta coupler of the general formula (II).

10. The color photographic light-sensitive material of claim 1, wherein said silver halide emulsion layer is a green-sensitive silver halide emulsion layer.

11. The color photographic light-sensitive material of claim 10, further including a blue-sensitive silver halide emulsion layer and a red-sensitive silver halide emulsion layer on said support.

12. The color photographic light-sensitive material of claim 1, wherein said magenta coupler of the formula (II) is present in an amount of $2 \times 10^{-3}$ to about 2 mol per mol of silver in the emulsion layer.

* * * * *